United States Patent
Yang

(10) Patent No.: US 8,980,106 B2
(45) Date of Patent: Mar. 17, 2015

(54) APPARATUS AND METHOD FOR SEPARATION OF WHOLE BLOOD INTO PLASMA OR SERUM AND CELLS

(75) Inventor: Tahua Yang, Woodridge, IL (US)

(73) Assignee: Abbott Laboratories, Abbott Park, IL (US)

( * ) Notice: Subject to any disclaimer, the term of this patent is extended or adjusted under 35 U.S.C. 154(b) by 735 days.

(21) Appl. No.: 12/968,872

(22) Filed: Dec. 15, 2010

(65) Prior Publication Data

US 2012/0152858 A1 Jun. 21, 2012

(51) Int. Cl.
*B01D 43/00* (2006.01)
*B01L 3/00* (2006.01)
*G01N 33/49* (2006.01)

(52) U.S. Cl.
CPC ...... *B01L 3/502761* (2013.01); *G01N 33/4915* (2013.01); *B01L 2200/0652* (2013.01); *B01L 2300/0816* (2013.01); *B01L 2300/0864* (2013.01)
USPC .......... 210/767; 210/511; 210/513; 210/542; 210/600; 422/502

(58) Field of Classification Search
USPC .......... 210/511, 513, 542, 600, 767; 422/502
See application file for complete search history.

(56) References Cited

U.S. PATENT DOCUMENTS

| | | |
|---|---|---|
| 5,186,844 A | 2/1993 | Burd et al. |
| 2005/0029190 A1 | 2/2005 | Effenhauser et al. |
| 2006/0204400 A1 | 9/2006 | Blattert et al. |
| 2008/0290037 A1 | 11/2008 | Liu |
| 2009/0014360 A1 | 1/2009 | Toner et al. |
| 2009/0029870 A1 | 1/2009 | Ward et al. |
| 2009/0048805 A1 | 2/2009 | Kaduchak et al. |
| 2009/0053106 A1 | 2/2009 | Wu et al. |
| 2009/0107909 A1 | 4/2009 | Kotera et al. |
| 2009/0147253 A1 | 6/2009 | Hartmann et al. |
| 2009/0158823 A1 | 6/2009 | Kaduchak et al. |
| 2009/0162887 A1 | 6/2009 | Kaduchak et al. |
| 2009/0188795 A1 | 7/2009 | Oakey et al. |
| 2011/0084033 A1* | 4/2011 | Rodriguez Villarreal et al. ............... 210/774 |

FOREIGN PATENT DOCUMENTS

| | | |
|---|---|---|
| WO | 2009086043 A2 | 7/2009 |
| WO | WO2009115575 A1 | 9/2009 |
| WO | 2009123555 A1 | 10/2009 |

OTHER PUBLICATIONS

International Search Report and Written Opinion for Application No. PCT/US2011/065252, mailed on Apr. 2, 2012, 13 pages.
Jaggi R.D., et al., "Microfluidic Depletion of Red Blood Cells from Whole Blood in High-Aspect-Ratio Microchannels," Microfluid Nanofluid, 2007, vol. 3, pp. 47-53.

(Continued)

*Primary Examiner* — Dirk Bass
(74) *Attorney, Agent, or Firm* — Hanley, Flight and Zimmerman LLC

(57) ABSTRACT

A microfluidic device comprising a flow channel that utilizes various principles of fluid dynamics to simplify the processes of preparing a sample prior to in vitro diagnostic analysis. A flow channel wherein flow conditions result in a Reynolds number no greater than about 2000, preferably no greater than about 1000, provides enhanced separation of blood cells from a liquid medium, i.e., serum or plasma.

28 Claims, 6 Drawing Sheets

(56) References Cited

OTHER PUBLICATIONS

Kersaudy-Kerhoas M., et al., "Validation of a Blood Plasma Separation System by Biomarker Detection," The Royal Society of Chemistry, 2010, vol. 10 (12), pp. 1587-1595.

Rodriguez-Villarreal AI., et al., "High Flow Rate Microfluidic Device for Blood Plasma Separation Using a Range of Temperatures," The Royal Society of Chemistry, 2010, vol. 10 (2), pp. 211-219.

Yang S., et al., "A Microfluidic Device for Continuous, Real Time Blood Plasma Separation," The Royal Society of Chemistry, 2006, vol. 6 (7), pp. 871-880.

Kersaudy-Kerhoas M., et al., "Hydrodynamic Blood Plasma Separation in Microfluidic Channels," Microfluidics and Nanofluidics, 2009, vol. 8 (1), pp. 105-114.

Armani M., et al., "Fabricating PDMS Microfluidic Channels Using a Vinyl Sign Plotter", Lab on a Chip Technology (vol. 1): Fabrication and Microfluidics, Herold K.E., et al., Eds., Caister Academic Press, Norfolk, UK, 2009, pp. 9-15.

Bersano-Begey T.F., et al., "Braille Microfluidics", Lab on a Chip Technology, vol. 2: Biomolecular Separation and Analysis, Herold K.E., et al., Eds., Caister Academic Press, Norfolk, UK, 2009, pp. 269-285.

Carlen E.T., et al., "Silicon and Glass Micromachining", Lab on a Chip Technology (vol. 1): Fabrication and Microfluidics, Herold K.E., et al., Eds., Caister Academic Press, Norfolk, UK, 2009, pp. 83-114.

Cheung Y.K., et al., "Microfluidics-based Lithography for Fabrication of Multi-Component Biocompatible Microstructures", Lab on a Chip Technology (vol. 1): Fabrication and Microfluidics, Herold K.E., et al., Eds., Caister Academic Press, Norfolk, UK, 2009, pp. 115-124.

Complete Blood Count—Wikipedia, the free encyclopedia, [online]. 2010 [retrieved on Mar. 9, 2011]. Retrieved from the Internet: <URL: http://en.wikipedia.org/wiki/Complete_blood_count>., pp. 1-5.

Erickson D., et al., "Introduction to Electrokinetic Transport in Microfluid Systems", Lab on a Chip Technology, vol. 1: Fabrication and Microfluidics, Herold K.E., et al., Eds., Caister Academic Press, Norfolk, UK, 2009, pp. 231-248.

Fan R., et al., "Integrated Blood Barcode Chips", National Biotechnology, 2008, vol. 26 (12), pp. 1373-1378 (14 pages).

Fourman J., et al., "The Effect of Intra-Arterial Cushions on Plasma Skimmimg in Small Arteries," Journal of Physiology, 1961, vol. 158, pp. 374-380.

Grover W.H., et al., "Monolithic Membrane Valves and Pumps", Lab on a Chip Technology, vol. 1: Fabrication and Microfluidics, Herold K.E., et al., Eds., Caister Academic Press, Norfolk, UK, 2009, pp. 285-317.

Hematocrit—Wikipedia, the free encyclopedia, [online]. 2010 [retrieved on Mar. 9, 2011]. Retrieved from the Internet < URL: http://en.wikipedia.org/wiki/Hematocrit>., pp. 1-3.

Hunt T.P., et al., "Integrated Circuit/Microfluidic Chips for Dielectric Manipulation", Lab on a Chip Technology, vol. 2: Biomolecular Separation and Analysis, Herold K.E., et al., Eds., Caister Academic Press, Norfolk, UK, 2009, pp. 187-206.

Jønsson V., et al., "Significance of plasma skimming and plasma volume expansion," Journal of Applied Physiology, 1992, vol. 72 (6), pp. 2047-2051.

Li M.W., et al., "Injection Schemes for Microchip-based Analysis Systems", Lab on a Chip Technology, vol. 1: Fabrication and Microfluidics, Herold K.E., et al., Eds., Caister Academic Press, Norfolk, UK, 2009, pp. 385-403.

Nguyen, Fundamentals and Applications of Microfluidics, 2nd Edition, Artech House, Inc., Norwood, MA, 2006, pp. 255-309.

Nguyen, Fundamentals and Applications of Microfluidics, 2nd Edition, Artech House, Inc., Norwood, MA, 2006, pp. 395-417.

Nguyen N.T., et al., Fundamentals and Applications of Microfluidics, 2nd Edition, Artech House, Inc., Norwood, MA, 2006, pp. 55-115.

Sun. S., et al., "Laminated Object Manufacturing (LOM) Technology-based MultiChannel Lab-on-a-Chip for Enzymatic and Chemical Analysis", Lab on a Chip Technology (vol. 1): Fabrication and Microfluidics, Herold K.E., et al., Eds., Caister Academic Press, Norfolk, UK, 2009, pp. 161-172.

Tabeling, Introduction to Microfabrication, Oxford University Press, Oxford, Great Britain, 2005, pp. 244-295.

Tsao C.W., et al., "Bonding Techniques for Thermoplastic Microfluidics", Lab on a Chip Technology (vol. 1): Fabrication and Microfluidics, Herold K.E., et al., Eds., Caister Academic Press, Norfolk, UK, 2009, pp. 45-63.

Waddell E., "Laser Micromachining", Lab on a Chip Technology (vol. 1): Fabrication and Microfluidics, Herold K.E., et al., Eds., Caister Academic Press, Norfolk, UK, 2009, pp. 173-184.

Yang S., et al., "Blood Plasma Separation in Microfluidic Channels Using Flow Rate Control," American Society for Artificial Internal Organs Journal, 2005, vol. 51, pp. 585-590.

\* cited by examiner

APPARATUS AND METHOD FOR SEPARATION OF WHOLE BLOOD INTO PLASMA OR SERUM AND CELLS

BACKGROUND OF THE INVENTION

1. Field of the Invention

This invention relates to the separation of particles from a liquid in which the particles are suspended, more particularly, the separation of blood cells from the blood plasma or the blood serum in which they are suspended.

2. Discussion of the Art

For in vitro diagnostics, biological samples currently used are samples of blood plasma or samples of blood serum. Samples of blood plasma and samples of blood serum are used because of potential physical interferences with detection (e.g., light scattering or absorption caused by blood cells) and chemical interferences caused by lysis of red blood cells (which alters the composition of the specimen). Disease markers related to proteins, lipoproteins, hormones, antibodies, antigens, viruses, bacteria, and parasites are commonly detected in blood plasma or blood serum of a patient. In order to collect blood plasma or blood serum, red blood cells, white blood cells, platelets, and other components must be removed from a sample of whole blood. Blood plasma makes up about 55% of total blood volume. It is composed mostly of water (90% by volume) and contains dissolved proteins, glucose, clotting factors, mineral ions, hormones, and carbon dioxide (plasma being the main medium for excretory product transportation). Blood serum is blood plasma without fibrinogen or the other clotting factors. Blood cells must be removed from blood plasma or blood serum before the sample of blood can be analyzed.

Centrifugation and filtration are currently used to separate blood cells from blood plasma or blood serum for diagnostic purposes. Both techniques require extensive labor and a relatively great amount of time for medical laboratories, which have limited resources with respect to both equipment and personnel. The drawbacks of centrifugation, wherein samples of whole blood are introduced into a centrifuge rotating at from about 1500 to about 3400 rpm, typically from about 3000 to about 3400 rpm, for 10 to 15 minutes, include consumption of time, which results from the time needed by a technician to load and unload samples and the need for a skilled technician to aspirate blood plasma or blood serum with a pipette from the separated layers in blood collection tubes. Up to 25% of the time consumed in medical laboratories involves centrifugation of samples. The drawbacks of filtration processes include fouling of the filter and low throughput after fouling occurs. A finite filter capacity and problems with non-specific binding on account of the large surface area of a filter are problematic with respect to filtration steps. Other potential problems include breakage of blood collection tubes and loss of the sample. There is also the risk of hemolysis and the consequent destruction of the sample. Accordingly, it would be desirable to provide a method that is cost effective and efficient for the separation of blood cells from blood plasma or blood serum in order to analyze a sample of blood.

Burd et al., U.S. Pat. No. 5,186,844, discloses an analytical rotor for separating cellular components from a biological fluid. The rotor includes a separation chamber spaced radially outward from the sample chamber. The sample chamber may be an open receptacle disposed to receive sample or may be a mixing chamber which receives sample and diluent. A flow restrictive channel connects the sample chamber to the separation chamber so that fluid enters the separation chamber at a controlled rate. The cellular components collect within a retention region located generally at the outer periphery of the collection chamber while cell-free fluid is continuously removed through a collection port. The collection is spaced annularly apart from the flow channel so that there is sufficient residence time within the separation chamber for substantially complete separation of the cells from the fluid fraction.

Effenhauser, et al., U.S. Patent Application Publication No. US 2005/0029190, discloses a method for separating particles from a fluid dispersion, particularly for separating corpuscular components from biological samples, above all, from blood. A separating module suitable for performing the method has a substrate with flow channels, comprising a feed channel for supplying the dispersion to a junction, a first drain channel for draining fluid having a reduced particle concentration away from the junction, and a second drain channel for draining fluid having an increased particle concentration away from the junction. The fluid flows so much faster in the second drain channel than in the first drain channel that due to different flow speeds the dispersed particles preferentially flow at the junction further in the second drain channel.

Blattert et al., U.S. Patent Application Publication No. US 2006/0204400, discloses a process for separation of dispersions or suspensions by applying an external pressure gradient between a feed reservoir and at least one waster reservoir in such a way that the dispersion flows into a microchannel system. At least one fraction is separated through an opening and via at least one target channel. Different flows in a waster channel and a target channel of the microchannel system are set by the selection of an external pressure gradient. The various phases in a dispersion or suspension are separated and concentrated further by a series arrangement of structures of bend arcs. An apparatus for carrying out the process connects the feed reservoir and at least one waste reservoir via a feed channel, at least one bend arc and further channels, respectively, the fractions of the dispersion or the suspension separated substantially within the at least one bend arc.

Fan et al., "Integrated Blood Barcode Chips", Nat Biotechnol. 2008 December; 26(12): 1373-1378, published online 2008 Nov. 16. doi: 10.1038/nbt.1507, discloses an integrated microfluidic system that enables on-chip blood separation and the rapid measurement of a panel of plasma proteins from small quantities of blood samples including a fingerprick of whole blood. The article discloses a polydimethylsiloxane (PDMS)-on-glass chip designed for 8-12 separate multi-protein assays to be executed sequentially, or in parallel, starting from whole blood. The plasma separation was achieved by exploiting the Zweifach-Fung effect of highly polarized blood cell flow at branch points of small blood vessels. This hydrodynamic effect was utilized by flowing blood through a low-flow-resistance primary channel that has high-resistance, centimeter long channels branching off perpendicularly. As the resistance ratio is increased between the branches and the primary channel, a critical streamline moves closer to the primary channel wall adjoining the branch channels. Blood cells with a radius larger than the distance between this critical streamline and the primary channel wall are directed away from the high-resistance channels, and about 15% of the plasma is skimmed into the high-resistance channels. The remaining whole blood is directed towards a waste outlet. The glass base of the plasma-skimming channels is pre-patterned, prior to the microfluidics chip assembly, with a dense barcode-like array of ssDNA oligomers. A full barcode is repeated multiple times within a single plasma-skimming channel, and each barcode sequence constitutes a complete assay.

SUMMARY OF THE INVENTION

This invention provides a microfluidic device and a method for using the microfluidic device. The microfluidic device comprises a flow channel that utilizes various principles of fluid dynamics to simplify the processes of preparing a sample prior to in vitro diagnostic analysis. It has discovered that a flow channel wherein flow conditions result in a Reynolds number no greater than about 2000 provides enhanced separation of blood cells from a liquid medium, i.e., serum or plasma.

In a preferred embodiment, the method for separating blood cells from serum or plasma comprises the steps of:
(a) providing a microfluidic device having at least a first end and a second end, the microfluidic device having at least one primary flow channel traversing at least a potion of the microfluidic device and running from a position at or near the first end of the microfluidic device to a position at or near the second end of the microfluidic device, the at least one primary flow channel having an inlet port at or near the first end of the microfluidic device and at least one outlet port at or near the second end of the microfluidic device, the at least one of said outlet ports at or near the second end of the microfluidic device for collecting serum or plasma;
(b) introducing a sample of whole blood into the inlet port;
(c) driving the sample through the at least one primary flow channel under such conditions that the flow of the sample is laminar; and
(d) recovering serum or plasma at least one of the outlet ports.

The microfluidic device described herein can be used in pre-analytical processes in medical laboratories, in point-of-care medical devices, and in microelectromechanical systems (MEMS).

Separation of components of a liquid composition by means of a flow channel in a microfluidic device utilizes devices that occupy a much smaller footprint than does a conventional clinical analyzer. Separation of components of a liquid composition by means of a flow channel in a microfluidic device only requires a normal syringe pump to deliver a liquid composition to the flow channel in a microfluidic device. Devices having a flow channel in a microfluidic device can be operated in a continuous mode with no capacity limitation, which is in contrast to separation by means of filtration or centrifugation. Separation of components of a liquid composition by means of a flow channel in a microfluidic device enables high throughput at greater than 100 mL/min. Devices for separation of components of a liquid composition by means of a flow channel in a microfluidic device can be easily integrated into designs for automated systems involving pre-analytics, which may involve one or more of the operations of centrifugation, decapping, aliquoting, recapping, barcode labeling, and sorting. Devices for separation of components of a liquid composition by means of a flow channel in a microfluidic device can be modified (e.g., scaled-down) for a point-of-care instrument platform.

DETAILED DESCRIPTION

Figure 1A:
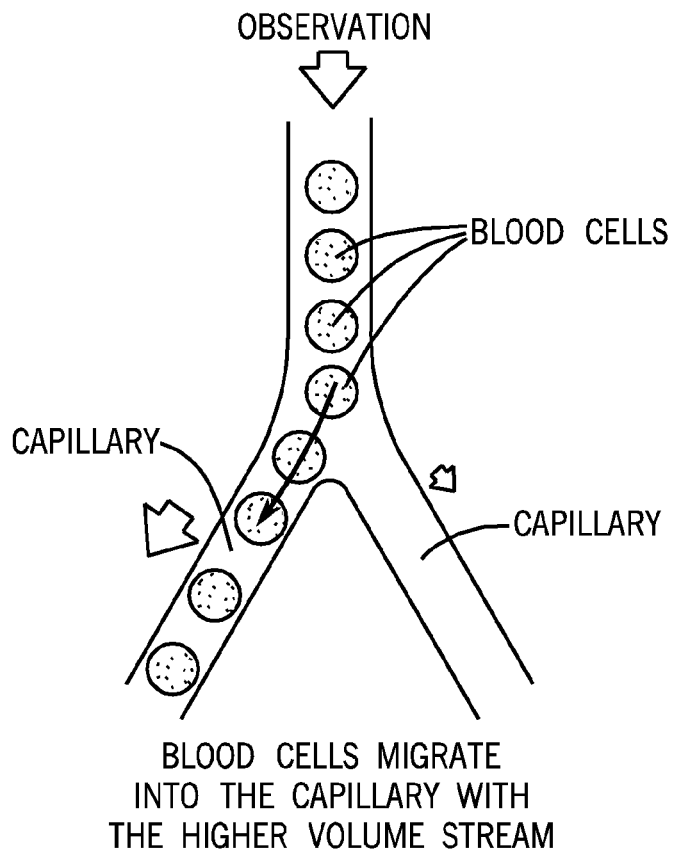
FIG. 1A is a schematic diagram illustrating the migration of blood cells in a bifurcated flow channel in a blood vessel.

As used herein, the expression "flow channel" means a tubular passage for liquids. As used herein, the expression "microfluidic device" means a physical element that enables the control and manipulation of fluids that are geometrically constrained to a small, typically sub-millimeter scale. Further discussion of microfluidics can be found at Microfluidics—Wikipedia, the free encyclopedia, [online]. 2010 [retrieved on 2010 Sep. 13]. Retrieved from the Internet: <URL: http://en.wikipedia.org/wiki/Microfluidics>, pages 1-7, incorporated herein by reference. Representative examples of materials that can be used to make microfluidic devices include, but are not limited to, silicone rubber, glass, plastic, silicon.

As used herein, the expression "Reynolds number" means $\rho \upsilon L / \mu$.

where
$\rho$ represents density of a liquid
$\upsilon$ represents velocity of the liquid
$L$ represents characteristic length of a flow channel
$\mu$ represents viscosity of the liquid As used herein, the phrase "critical Reynolds number" means a Reynolds number of approximately 2000. At a Reynolds number below about 2000, the flow of the fluid is laminar. At a Reynolds number above about 2000, the flow of the fluid is turbulent. The Reynolds number of blood flowing in the blood vessels in the aorta artery is approximately 1000. The Reynolds number of blood flowing in the blood vessels of the arteries of the brain is approximately 100.

As used herein, the term "furcated' means divided into branches. As used herein, the term "branch" means a limited part of a larger or more complex body, i.e., a smaller flow channel emerging from a primary flow channel or entering or re-entering a primary flow channel. As used herein, the term "primary flow channel" means a flow channel through which at least a majority of the sample flows.

As used herein, the term "hematocrit" means the proportion of blood volume that is occupied by red blood cells. It is normally about 48% for men and 38% for women. With modern laboratory equipment, the hematocrit is calculated by an automated analyzer and not directly measured. Hematocrit is determined by multiplying red cell count by the mean cell volume. Additional information relating to the meaning of the term "hematocrit" can be found at Complete blood count—Wikipedia, the free encyclopedia, [online]. 2010 [retrieved on 2010 Dec. 9]. Retrieved from the Internet: <URL: http://en.wikipedia.org/wiki/Complete_blood_count>, pages 1-5, and Hematocrit—Wikipedia, the free encyclopedia, [online]. 2010 [retrieved on 2010 Dec. 9]. Retrieved from the Internet: <URL: http://en.wikipedia.org/wiki/Hematocrit>, pages 1-3, both of which are incorporated herein by reference Certain parameters are involved in the determination of Reynolds number. These parameters include the density of a liquid and the viscosity of a liquid. The density of plasma is approximately 1.025 g/cc. The density of blood cells is approximately 1.125 g/cc.

The viscosity of plasma is approximately 1.14 cp. If the value of hematocrit is 20%, the viscosity of the plasma is 3 cp. If the value of hematocrit is 30%, the viscosity of the plasma is 4 cp. If the value of hematocrit is 60%, the viscosity of the plasma is 8 cp.

Assuming that a rectangular flow channel has a height of 100 micrometers and a width of 2 centimeters, a flow velocity of 1 meter/second leads to a Reynolds number of 13.75 for value of hematocrit of 60%. (Flow rate=0.01 cm×2 cm×100 cm/sec=2 cm$^3$/sec (2 mL/sec or 120 mL/min)

Figure 1B:
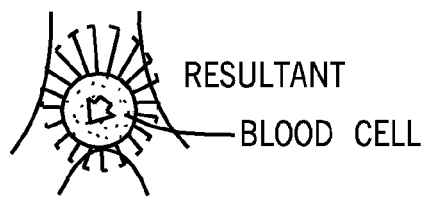
FIG. 1B is a schematic diagram illustrating the forces acting upon a blood cell approaching the point at which a blood vessel branches into two capillaries.
Figure 1C:
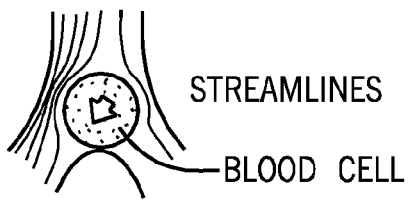
FIG. 1C is a schematic diagram illustrating the effect of streamlines adjacent to a blood cell approaching the point at which a blood vessel branches into two capillaries.
Figure 1D:
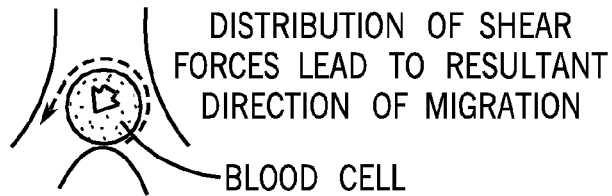
FIG. 1D illustrates the distribution of shear forces leading to the resultant direction of migration of a blood cell traveling in a blood vessel.

In biological systems, blood cells being transported in blood vessels tend to migrate toward the center of the vessels and leave the region adjacent to the vessel wall rich in plasma on account of a non-uniform velocity profile. This phenomenon is known as plasma skimming. When a blood vessel branches in two, blood cells tend to move in the branch having the higher flow velocity and leave the branch having the lower flow velocity, thereby leaving the latter branch with enriched plasma. This phenomenon, which is typically observed in cardiovascular bifurcation branches, is illustrated in FIG. 1A. See for example, Fourman et al., "THE EFFECT OF INTRA-ARTERIAL CUSHIONS ON PLASMA SKIMMING IN SMALL ARTERIES", *J. Physiol.* (1961), 158, pp. 374-380; Jönsson et al., "Significance of plasma skimming and plasma volume expansion", J. Appl. Physiol. 72(6): 2047-2051, 1992; Yang et al., "Blood Plasma Separation in Microfluidic Channels Using Flow Rate Control", *ASAIO Journal* 2005; 51:585-590, all of which are incorporated herein by reference. FIG. 1B illustrates the forces acting upon a blood cell approaching the point at which a blood vessel branches into two capillaries. FIG. 1C illustrates the effect of streamlines adjacent to a blood cell approaching the point at which a blood vessel branches into two capillaries. FIG. 1D illustrates the distribution of shear forces leading to the resultant direction of migration of a blood cell traveling in a blood vessel.

Because of velocity profile in the path of flow when the liquid is flowing under laminar conditions, blood cells move toward the high velocity region. Bifurcation of the path of flow allows for collection of plasma through the branches in the path of flow. Moreover, collection of plasma can be further enhanced by differential flow rates among the branches in the path of flow.

Separation of components in a flow channel in a microfluidic device is based on a hydrodynamic mechanism, in contrast with centrifugation, where separation is based upon density, and filtration, where separation is based upon exclusion based on size of particles or upon exclusion based on shape of particles.

Figure 2:
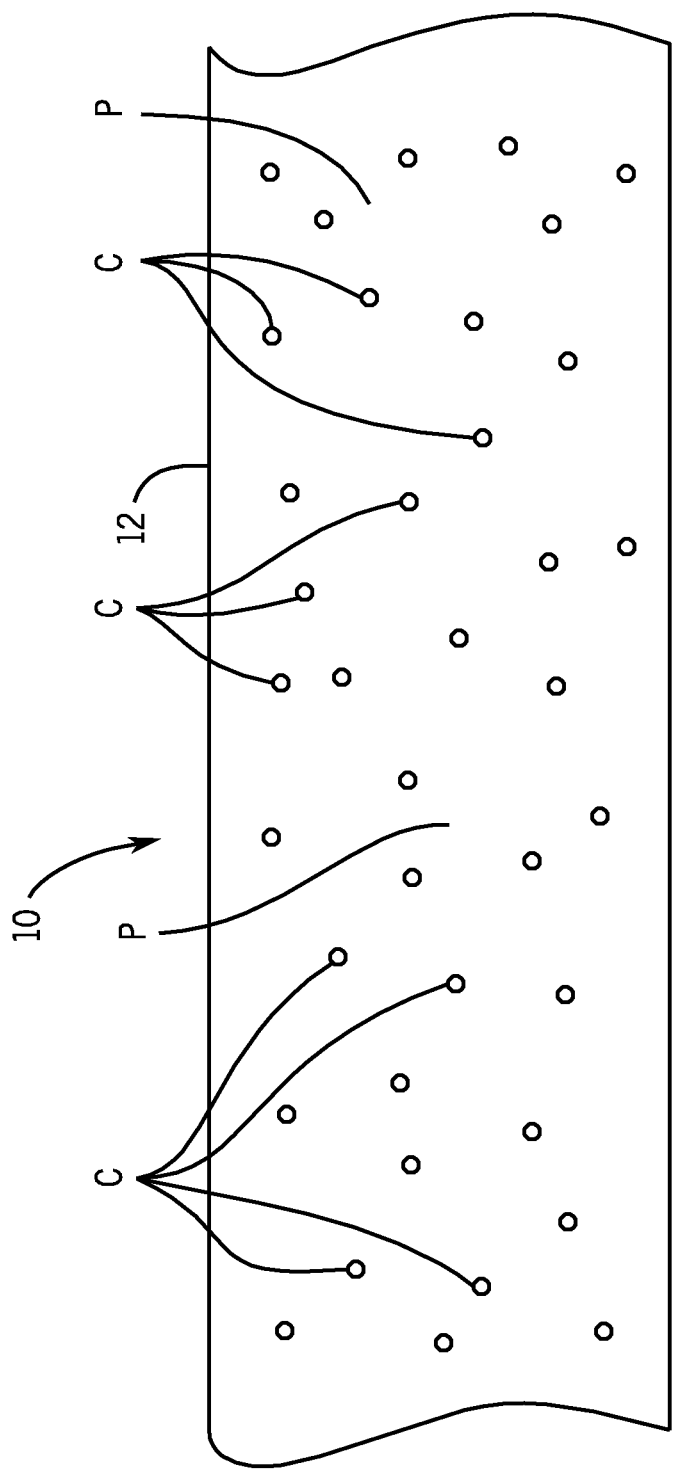
FIG. 2 is a schematic diagram illustrating the flow of blood cells in a liquid medium, i.e., serum or plasma, through a flow channel of a microfluidic device. The schematic diagram represents a side view in elevation of the flow channel.
Figure 3:
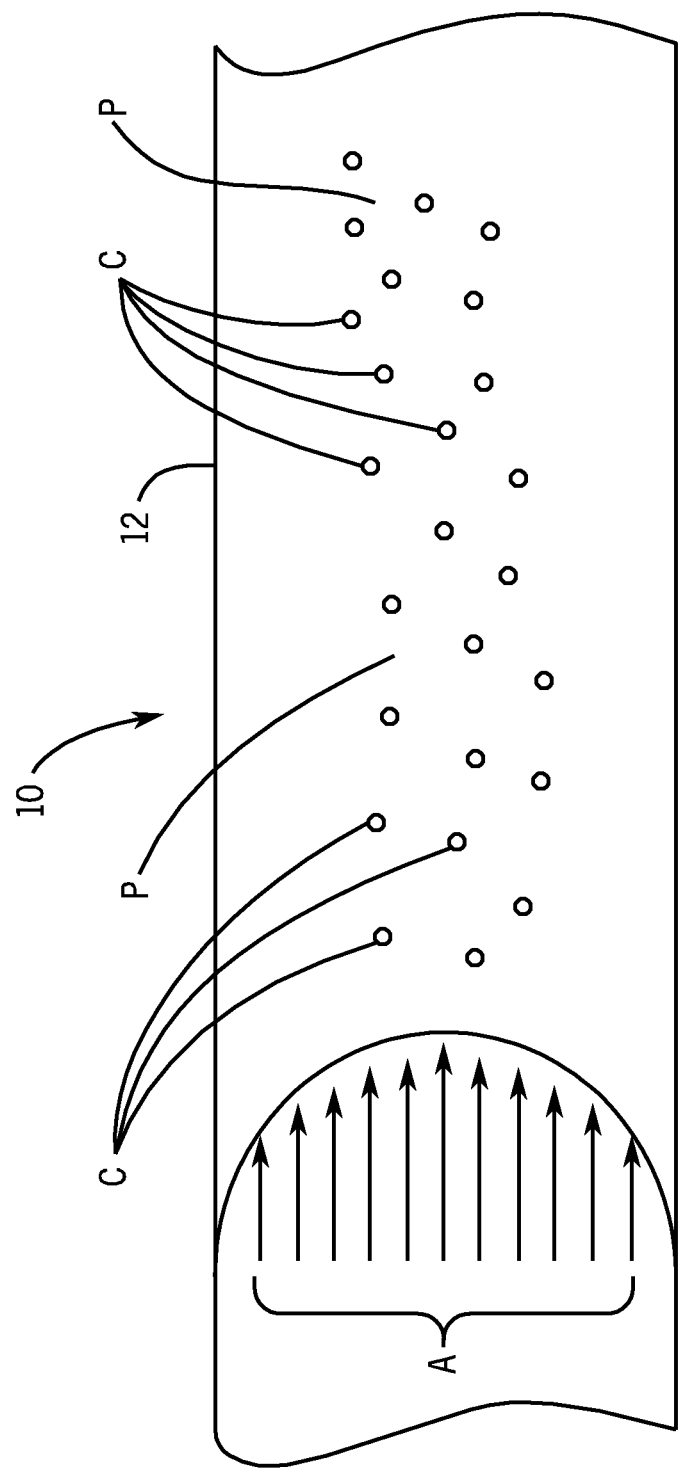
FIG. 3 is another schematic diagram illustrating the phenomenon of plasma skimming the flow channel of the microfluidic device of FIG. 2. The schematic diagram represents a side view in elevation of the flow channel.

Referring now to FIGS. 2 and 3, a microfluidic device 10 comprises a flow channel 12. In the flow channel 12 is a sample of blood. The sample of blood comprises cells "C" and plasma "P." The dimensions of the flow channel 12 are, for example, approximately 0.01 cm in height by 2 cm in width. Under conditions of laminar flow, the cells "C" migrate toward the center of the flow channel 12. FIG. 2 shows blood cells "C" suspended in plasma 'P." FIG. 3 shows blood cells "C" migrating toward the center of the flow channel 12. Arrows "A" indicate the direction of flow of the sample of blood.

Figure 4:
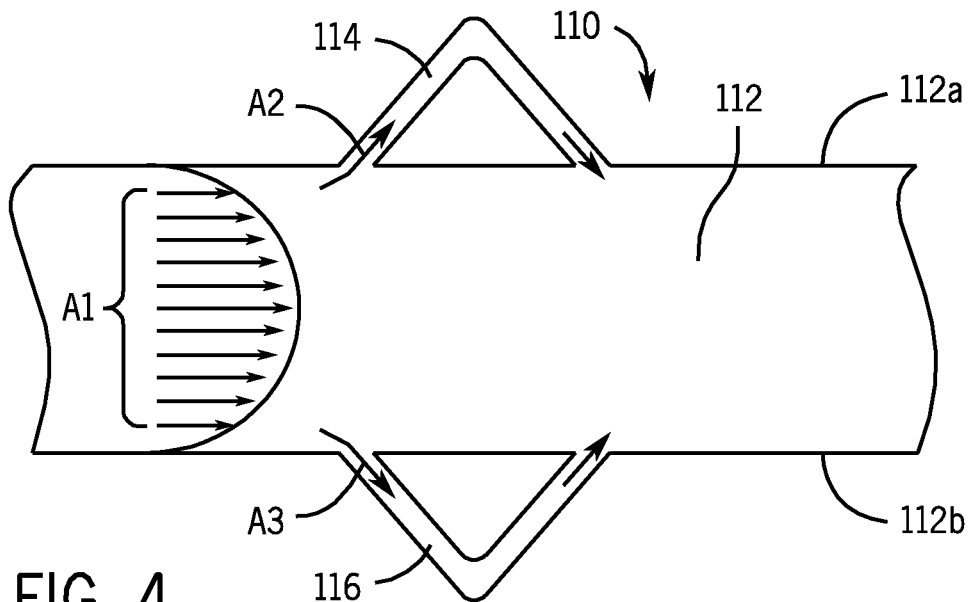
FIG. 4 is a schematic diagram illustrating one embodiment of a furcated flow channel in a microfluidic device. The schematic diagram represents a side view in elevation of the furcated flow channel.

FIG. 4 illustrates a microfluidic device 110 having a primary flow channel 112. However, the primary flow channel 112 is furcated in such a manner that a first branch 114 emerges from the wall 112a of the flow channel 112 and a second branch 116 emerges from the wall 112b of the primary flow channel 112. In addition, the first branch 114 and the second branch 116 are designed so as to re-enter the primary flow channel 112 via the wall 112a and the wall 112b, respectively. In FIG. 4, the first branch 114 and the second branch 116 are substantially L-shaped. Arrows A1, A2, and A3 indicate the proposed direction of flow of a sample of blood. It should be noted that it is not necessary for a branch to re-enter the primary flow channel 112. It should also be noted that fewer than two branches and more than two branches can be connected to the primary flow channel 112.

Figure 5:
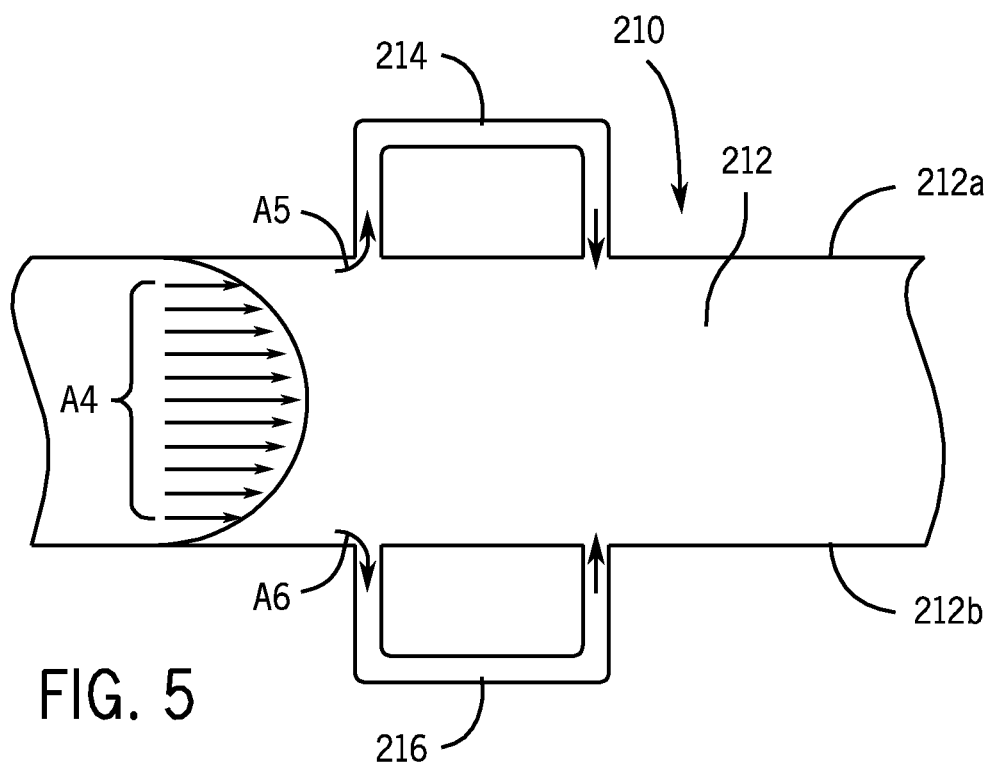
FIG. 5 is a schematic diagram illustrating another embodiment of a furcated flow channel in a microfluidic device. The schematic diagram represents a side view in elevation of the furcated flow channel.

FIG. 5 illustrates a microfluidic device 210 having a primary flow channel 212. However, the primary flow channel 212 is furcated in such a manner that a first branch 214 emerges from the wall 212 a of the primary flow channel 212 and a second branch 216 emerges from the wall 212 b of the primary flow channel 212. In addition, the first branch 214 and the second branch 216 are designed so as to re-enter the primary flow channel 212 via the wall 212 a and the wall 212 b, respectively. In FIG. 5, the first branch 214 and the second branch 216 are substantially rectilinear-shaped. Arrows A4, A5, and A6 indicate the proposed direction of flow of a sample of blood. It should be noted that it is not necessary for a branch to re-enter the primary flow channel 212. It should also be noted that fewer than two branches and more than two branches can be connected to the primary flow channel 212.

Figure 6:
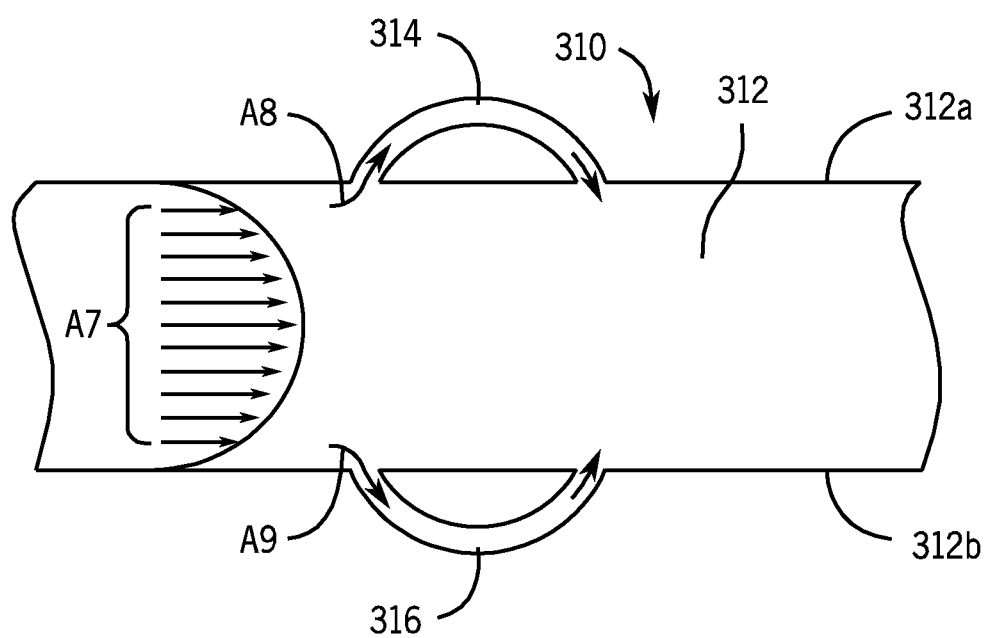
FIG. 6 is a schematic diagram illustrating still another embodiment of a furcated flow channel in a microfluidic device. The schematic diagram represents a side view in elevation of the furcated flow channel.

FIG. 6 illustrates a microfluidic device 230 having a primary flow channel 312. However, the primary flow channel 312 is furcated in such a manner that a first branch 314 emerges from the wall 312a of the flow channel 312 and a second branch 316 emerges from the wall 312b of the primary flow channel 312. In addition, the first branch 314 and the second branch 316 are designed so as to re-enter the primary flow channel 312 via the wall 312a and the wall 312b, respectively. In FIG. 6, the first branch 314 and the second branch 316 are substantially curvilinear-shaped. Arrows A7, A8, and A9 indicate the proposed direction of flow of a sample of blood. It should be noted that it is not necessary for a branch to re-enter the primary flow channel 312. It should also be noted that fewer than two branches and more than two branches can be connected to the primary flow channel 312.

Figure 7:
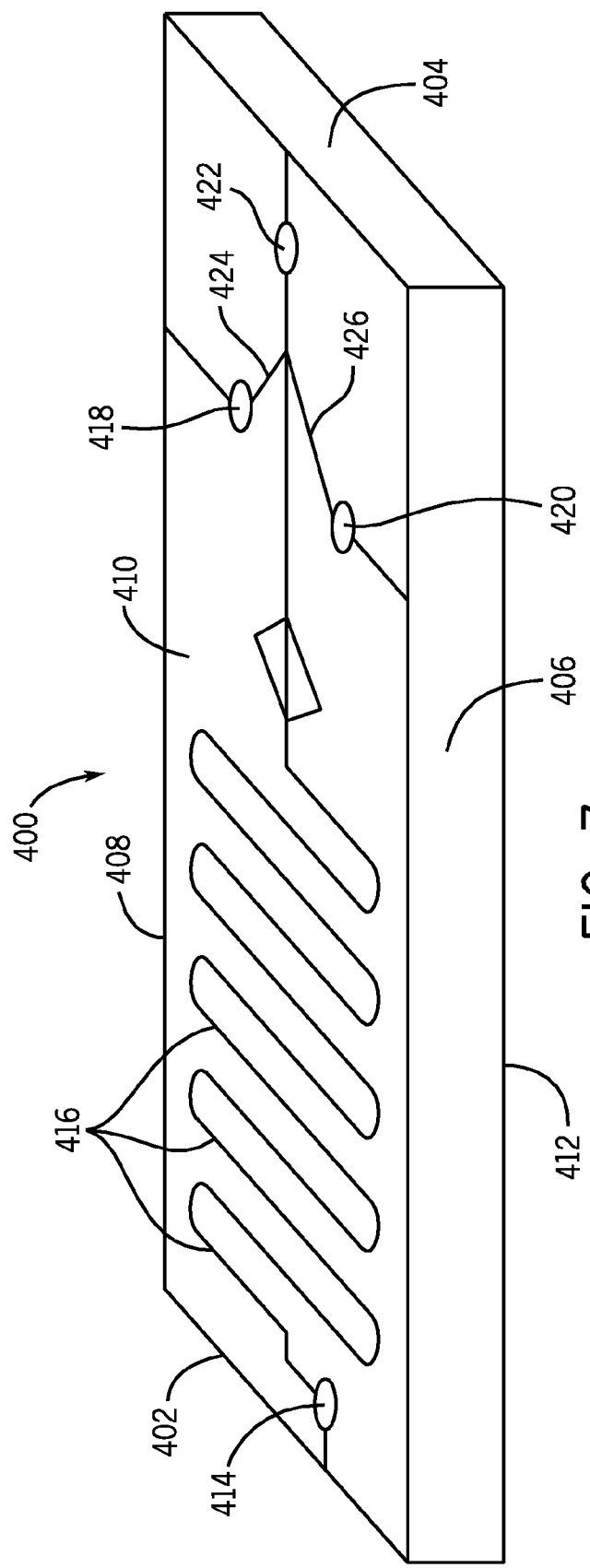
FIG. 7 is a schematic diagram illustrating a perspective view of a microfluidic device that is capable of carrying out the method described herein.

FIG. 7 illustrates a perspective view of a microfluidic device that is capable of carrying out the method described herein. The microfluidic device 400 has a first end 402, a second end 404, a first side 406, a second side 408, a top surface 410, and a bottom surface 412. As shown in FIG. 7, the microfluidic device 400 is constructed of a transparent material, typically a transparent polymeric material. The microfluidic device 400 has an inlet port 414, a primary flow channel 416, a first outlet port 418, a second outlet port 420, a region 422 for concentrating blood cells, a first branch 424 of the primary flow channel 416, and a second branch 426 of the primary flow channel 416.

In order to use the microfluidic device for separating plasma from cells in a sample of whole blood, a sample of whole blood is introduced into the inlet port 414. The sample of whole blood blows through the primary flow channel 416 at such a flow rate that the Reynolds number of the fluid does not exceed 2000, and preferably does not exceed 1000. It is preferred that the Reynolds number not exceed 1000 in order to avoid hemolysis of blood cells. The plasma is skimmed from the cells as the sample of whole blood flows through the primary flow channel 416. At least a portion of the primary flow channel 416 is sinuous in form. The plasma is then removed at the first outlet port 418 and at the second outlet port 420. The blood cells can be collected at the region 422 for concentrating blood cells. By the use of branches 424 and 426 in the microfluidic device in order to remove portions of plasma, efficiency of separation of plasma from blood cells can be improved. The region 422 of the microfluidic device downstream of the primary flow channel 416 enables the collection of cells at a higher concentration than in the sample of blood, thereby further enhancing efficiency of separation of plasma from blood cells. In microfluidic devices, the inertia of the flow of the sample is not likely to affect the pattern of the flow of the sample. The orientation of the first branch 424 and the second branch 426 facilitates positioning of collection devices (not shown). It is preferred that the devices for collecting plasma and cells not interfere with each other.

The sample can be driven by the force of capillary attraction. Alternatively, the sample can be driven a pump, by electrical forces, or by other means for driving samples. Pumps include, but are not limited to, rotary (centrifugal) pumps; peristaltic pumps; and ultrasonic pumps. Electrical forces include, but are not limited to, electrohydrodynamic forces; electrokinetic forces, e.g., electrophoresis, electroosmosis; and surface tension driven, e.g., electrowetting, electrowetting on dielectric surface. Means for driving samples are discussed in greater detail in (1) Nguyen et al., *Fundamentals and Applications of Microfluidics*, Second Edition, ARTECH HOUSE, INC. (Norwood, Mass.: 2006), pages 255-309; (2) Erickson et al., Introduction to Electrokinetic Transport in Microfluidic Systems, *Lab on a Chip Technology, Volume 1: Fabrication and Microfluidics*, edited by Herold et al., Caister Academic Press (Norfolk, UK: 2009), pages 231-248; (3) Grover et al., Monolithic Membrane Valves and Pumps, *Lab on a Chip Technology, Volume 1: Fabrication and Microfluidics*, edited by Herold et al., Caister Academic Press (Norfolk, UK: 2009), pages 285-317; (4) Hunt et al., Integrated Circuit/Microfluidic Chips for Dielectric Manipulation, *Lab on a Chip Technology, Volume 2: Biomolecular Separation and Analysis*, edited by Herold et al., Caister Academic Press (Norfolk, UK: 2009), pages 187-206, (5) Bersano-Begey et al., Braille Microfluidics, *Lab on a Chip Technology, Volume 2: Biomolecular Separation and Analysis*, edited by Herold et al., Caister Academic Press (Norfolk, UK: 2009), pages 269-285, all of which are incorporated herein by reference. Nguyen et al. discusses microvalves, micropumps, microflow sensors, microfilters and microseparators in detail. The chapters in Herold et al. discuss valves, pumps, and separation in detail.

The sample can be introduced to a flow channel of a microfluidic device by means of a syringe, by dipping the device into the sample, or other means. Other means for introducing a sample into a flow channel of a microfluidic device include microdispensers, e.g., droplet dispensers, such as, for example, injection nozzles; in-channel dispensers, e.g., metering dispensers. Means for introducing samples into a flow channel of a microfluidic device are discussed in greater detail in (1) Nguyen et al., *Fundamentals and Applications of Microfluidics*, Second Edition, ARTECH HOUSE, INC. (Norwood, Mass.: 2006), pages 395-417; (2) Li et al., Injection Schemes for Microchip-based Analysis Systems, *Lab on a Chip Technology, Volume 1: Fabrication and Microfluidics*, edited by Herold et al., Caister Academic Press (Norfolk, UK: 2009), pages 385-403, both of which are incorporated herein by reference. Nguyen et al. discusses microdispensers in detail. Herold et al. discusses microdispensers in detail.

Dimensions of microfluidic devices and the flow channels thereof, and the materials for constructing microfluidic devices and methods for constructing microfluidic devices are described in (1) Nguyen et al., *Fundamentals and Applications of Microfluidics*, Second Edition, ARTECH HOUSE, INC. (Norwood, Mass.: 2006), pages 55-115; (2) Tabeling, *Introduction to Microfluidics*, Oxford University Press (Oxford, Great Britain: 2005), pages 244-295; (3) Armani et al., Fabricating PDMS Microfluidic Channels Using a Vinyl Sign Plotter, *Lab on a Chip Technology, Volume 1: Fabrication and Microfluidics*, edited by Herold et al., Caister Academic Press (Norfolk, UK: 2009), pages 9-15; (4) Tsao et al., Bonding Techniques for Thermoplastic Microfluidics, *Lab on a Chip Technology, Volume 1: Fabrication and Microfluidics*, edited by Herold et al., Caister Academic Press (Norfolk, UK: 2009), pages 45-63; (5) Carlen et al., Silicon and Glass Micromachining, *Lab on a Chip Technology, Volume 1: Fabrication and Microfluidics*, edited by Herold et al., Caister Academic Press (Norfolk, UK: 2009), pages 83-114; (6) Cheung et al., Microfluidics-based Lithography for Fabrication of Multi-Component Biocompatible Microstructures, *Lab on a Chip Technology, Volume 1: Fabrication and Microfluidics*, edited by Herold et al., Caister Academic Press (Norfolk, UK: 2009), pages 115-138; (7) Sun et al., Laminated Object Manufacturing (LOM) Technology-Based Multi-Channel Lab-on-a-Chip for Enzymatic and Chemical Analysis, *Lab on a Chip Technology, Volume 1: Fabrication and Microfluidics*, edited by Herold et al., Caister Academic Press (Norfolk, UK: 2009), pages 161-172; Waddell, Laser Micromachining, *Lab on a Chip Technology, Volume 1: Fabrication and Microfluidics*, edited by Herold et al., Caister Academic Press (Norfolk, UK: 2009), pages 173-184, all of which are incorporated herein by reference.

The nature of the flow, i.e., laminar rather than turbulent, can be ensured by optimizing the dimensions of the flow channel of the microfluidic device with both the force driving the sample and the parameters of introducing the sample into the flow channel. Optimization can be carried out buy one of ordinary skill in the art.

Separation of components of a liquid composition by means of a flow channel in a microfluidic device utilizes devices that occupy a much smaller footprint than does a conventional clinical analyzer. Separation of components of a liquid composition by means of a flow channel in a microfluidic device only requires a normal syringe pump to deliver a liquid composition to the flow channel in a microfluidic device. Devices having a flow channel in a microfluidic device can be operated in a continuous mode with no capacity limitation, which is in contrast to separation by means of filtration or centrifugation. Separation of components of a liquid composition by means of a flow channel in a microfluidic device enables high throughput at greater than 100 mL/min. Devices for separation of components of a liquid composition by means of a flow channel in a microfluidic device can be easily integrated into designs for automated systems involving pre-analytics, which integrate two or more of centrifugation, decapping, aliquoting, recapping, barcode labeling, and sorting. Devices for separation of components of a liquid composition by means of a flow channel in a microfluidic device can be modified (e.g., scaled-down) for a point-of-care instrument platform.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A microfluidic device comprising:
   a first end;
   a second end opposite the first end; and
   a flow channel traversing at least a portion of the microfluidic device from a first position at or near the first end to a second position at or near the second end, the flow channel comprising:
     an inlet port at or near the first end;
     a first section having a plurality of turns;
     a second section having a substantially linear section, the flow channel at the linear section furcated into a primary flow channel and a branch, the branch re-entering the primary flow channel;
     a first outlet channel coupled to the linear section; and
     a first outlet port coupled to the first outlet channel at or near the second end to collect at least a portion of serum or plasma from a sample of blood comprising cells, serum and plasma that was introduced into the inlet port.

2. The microfluidic device of claim 1, wherein a cross-sectional area of the flow channel is no greater than about 0.02 centimeters squared ($cm^2$).

3. The microfluidic device of claim 1, wherein the branch is substantially L-shaped.

4. The microfluidic device of claim 1, wherein the branch is substantially rectilinear-shaped.

5. The microfluidic device of claim 1, wherein the branch is substantially curvilinear-shaped.

6. The microfluidic device of claim 1, wherein the flow channel further comprises:
   a second outlet port; and
   a second outlet channel connecting the linear section of the flow channel to the second outlet port.

7. The microfluidic device of claim 1, wherein the microfluidic device comprises at least one region for concentrating cells.

8. The microfluidic device of claim 1, wherein the branch is a first branch, further comprising a second branch emerging from the flow channel and reentering the flow channel.

9. The microfluidic device of claim 8, wherein the first branch emerges from a first wall of the primary flow channel and reenters the primary flow channel on the first wall.

10. The microfluidic device of claim 9, wherein the second branch emerges from a second wall of the flow channel, opposite the first wall, and reenters the primary flow channel on the second wall.

11. The microfluidic device of claim 1, wherein the flow channel has a first diameter for a first distance between the inlet port and the branch and the branch has a second diameter.

12. The microfluidic device of claim 11, wherein the flow channel further comprises a collection region to collect blood cells from the sample of whole blood that was introduced into the inlet port, and wherein the first distance of the flow channel between the inlet port and the branch is longer than a second distance of the flow channel between the branch and the collection region.

13. The microfluidic device of claim 12, wherein the flow channel has the first diameter between the inlet port and the collection region.

14. A method comprising:
   introducing a sample of whole blood into an inlet port of a microfluidic device, the sample of whole blood comprising blood cells, plasma and serum, the microfluidic device having a primary flow channel traversing between the inlet port and a first branch leading to an outlet port;
   directing the sample through a first section of the primary flow channel in a first direction;
   directing the sample through a second section of the primary flow channel in a second direction opposite the first direction, the second section parallel to and offset from the first section;
   directing the sample through a third section of the primary flow channel in the first direction, the third section parallel to and offset from the first and second sections;
   directing the sample through a fourth section of the primary flow channel;
   directing a portion of the sample flowing through the fourth section of the primary flow channel into a secondary flow channel;
   directing the portion of the sample back into the primary flow channel; and
   collecting the plasma and serum from the outlet port.

15. The method of claim 14, wherein the fourth section directs the sample in a third direction, the third direction perpendicular to the first direction, further comprising directing a portion of the sample containing the plasma and the serum into the first branch toward the outlet to separate the plasma and the serum from the whole blood, the first branch extending from the fourth section.

16. The method of claim 15, wherein the fourth section is between the third section and the first branch.

17. The microfluidic device of claim 1, wherein the first outlet channel leading from the linear section to the first outlet port is closer to the second end than a middle of the microfluidic device.

18. The method of claim 14, wherein a Reynolds number of the sample when flowing is below about 2000.

19. The method of claim 14, wherein a Reynolds number of the sample when flowing is below about 1000.

20. The method of claim 14, wherein the method is to operate in a continuous mode.

21. The method of claim 14 further comprising pumping the sample through the primary flow channel at a rate of at least about 100 milliliters (mL) per minute.

22. The method of claim 14, wherein a cross-sectional area of the primary flow channel is no greater than about 0.02 centimeters squared ($cm^2$).

23. The method of claim 14, wherein the secondary flow channel is substantially L-shaped.

24. The method of claim 14, wherein the secondary flow channel is substantially rectilinear-shaped.

25. The method of claim 14, wherein the secondary channel is substantially curvilinear-shaped.

26. The method of claim 14, wherein a portion of the primary flow channel comprising the first, second and third sections is sinuous.

27. The method of claim 14, wherein the microfluidic device further comprises a second branch leading to a second outlet port.

28. The method of claim 14 further comprising directing the whole blood after the third section to a region for concentrating cells.

* * * * *